(12) United States Patent
Horton

(10) Patent No.: US 7,901,439 B2
(45) Date of Patent: Mar. 8, 2011

(54) ALLOGRAFT SPINAL FACET FUSION SYSTEM

(76) Inventor: Kenneth L. Horton, Birmingham, AL (US)

( * ) Notice: Subject to any disclaimer, the term of this patent is extended or adjusted under 35 U.S.C. 154(b) by 505 days.

(21) Appl. No.: 11/831,611

(22) Filed: Jul. 31, 2007

(65) Prior Publication Data

US 2008/0255667 A1    Oct. 16, 2008

Related U.S. Application Data

(60) Provisional application No. 60/911,683, filed on Apr. 13, 2007.

(51) Int. Cl.
*A61B 17/88* (2006.01)
(52) U.S. Cl. .............. 606/279; 606/96; 606/99
(58) Field of Classification Search .... 623/17.11–17.16; 606/246–249, 279, 86 A, 96–100, 79, 80, 606/90, 104
See application file for complete search history.

(56) References Cited

U.S. PATENT DOCUMENTS

| | | | | |
|---|---|---|---|---|
| 4,877,020 A | * | 10/1989 | Vich | 606/86 R |
| 5,906,616 A | * | 5/1999 | Pavlov et al. | 606/247 |
| 6,158,437 A | * | 12/2000 | Vagley | 128/898 |
| 6,200,322 B1 | * | 3/2001 | Branch et al. | 606/96 |
| 6,371,988 B1 | * | 4/2002 | Pafford et al. | 623/17.11 |
| 7,445,636 B2 | * | 11/2008 | Michelson | 623/17.15 |
| 2006/0116688 A1 | * | 6/2006 | Boyd et al. | 606/90 |

* cited by examiner

*Primary Examiner* — Eduardo C Robert
*Assistant Examiner* — Christina Negrelli
(74) *Attorney, Agent, or Firm* — Kenneth M. Bush; Bush Intellectual Property Law

(57) ABSTRACT

A method for fusing a spinal facet joint and a surgical kit for use therein. The kit preferably comprises an allograft implant, a facet finder, a drill, a drill guide, and an implant inserter. The method preferably comprises the steps of locating the facet joint with a facet finer, sliding a drill guide over the facet finder until the drill guide engages the facet joint, removing the facet finder from within the drill guide, inserting a drill through the drill guide and drilling a socket within the facet joint to a predetermined depth, removing the drill from within the drill guide, securing an allograft implant within an implant inserter, inserting the implant inserter through the drill guide until the implant engages the socket, tapping the implant inserter to push the implant completely within the socket, removing the implant inserter from within the drill guide, and removing the drill guide.

6 Claims, 2 Drawing Sheets

ALLOGRAFT SPINAL FACET FUSION SYSTEM

REFERENCE TO RELATED APPLICATION

The present application claims priority to U.S. Provisional Application No. 60/911,683, filed on Apr. 13, 2007, the disclosure of which is incorporated herein by reference.

FIELD OF THE INVENTION

The present invention relates to surgical implant systems, and more particularly, to allograft implant methods used to fuse spinal vertebrae sod surgical kits therefor.

BACKGROUND OF THE INVENTION

A common surgical invention is spine fusion, in which two or more adjacent vertebral bodies are fused together in order to alleviate pain associated with the disc(s) located between those vertebral bodies. While spine fusion generally helps to eliminate certain types of pain, it has also been shown to decrease function by limiting the range of motion for patients in flexion, extension, rotation and lateral bending. Furthermore, it is believed that spine fusion creates increased stresses on adjacent non-fused motion segments. Also, the fusion device used to effect fusion, whether artificial or biological, may migrate out of the fusion site.

Posterior elements called facet joints, the small joints located behind adjacent vertebrae in the spine that allow for spinal motion, help to support axial, torsional and shear loads that act on the spinal column. The facet joints are diarthroidal joints that provide both sliding articulation and load transmission features. The facet's articular surfaces contact in extension, limiting rotation and increasing compressive load. The articular surfaces also contact on one side of the spine in lateral bending and axial rotation, also limiting rotation and transferring load. However, one of the root causes of back pain, particularly the persistent and disabling kind, is facet joints. The articular cartilaginous surfaces can degenerate due to mechanical or biological factors and cause pain as with other joint osteoarthritis. For example, a patient may suffer foam arthritic facet joints, severe facet joint tropism or otherwise deformed facet joints, facet joint injuries, etc. Furthermore, problems with the facet joints can also complicate treatments associated with other portions of the spine. There is currently a lack of suitable intervention procedures for facet joint disorders. Facetectomy, the removal of the facet joints, may provide some relief, but is also believed to significantly decrease the stiffness of the spinal column in all planes of motion.

There are several types of metal facet screws for fusion of facet joints but the metal screws compromise a large surface area of the facet, predisposing the facet to fracture. Consequently, the use of metal screws for fusion of facet joints is risky. The angle of insertion of the metal screw must be perfect. The use of pre-shaped, harvested or synthetic bone as a structural fixation for facet joint fusion offers three distinct advantages over pedicle or compression screws, which are presently used in facet fusion procedures: (1) using bone instead of metal allows for natural bone in-growth and a stronger, permanent fusion; (2) the natural or synthetic graft cannot work its way loose over time, a concern with screw type fixation; and, (3) the graft is self-leveling, which eliminates any concern of vertebral tilting. Tapered allograft dowels are known but there is nothing on those devices to prevent their migration from the place of insertion. Other types of allograft dowels have threads, but the threads tend to break. Interference allograft screws are known but are not suitable for use with facets. A molly bolt-type fusion mechanism with a gun inserter is known but does not provide the surgeon sufficient control when working with the spine.

What is needed, and is not found in the prior art, is an allograft facet fusion system that overcomes the disadvantages of prior art facet fusion systems.

SUMMARY OF THE INVENTION

The present invention comprises a surgical kit for use in a method for fusing a spinal facet joint preferably comprising an allograft implant, a facet finder, a facet finder guide, a drill, a drill guide, a mallet, an implant loader, and an implant inserter. The invention further comprises a method for fusing a spinal facet joint with an implant, preferably comprising the steps of locating the facet joint with a facet finder, sliding a drill guide over the facet finder until a distal end of the drill guide engages the facet joint, tapping a proximal end of the drill guide to reversibly secure the distal end of the drill guide to the facet joint, removing the facet finder from within the drill guide, inserting a drill through the drill guide and drilling a socket within the facet joint to a predetermined depth, removing the drill from within the drill guide, securing a proximal end of an allograft implant within a distal end of an implant inserter, inserting the implant inserter through the drill guide until a distal end of the implant inserter engages the socket, tapping a proximal end of the implant inserter to push the implant completely within the socket, removing the implant inserter from within the drill guide, and removing the drill guide.

These and other features of the invention will become apparent from the following detailed description of the preferred embodiments of the invention.

DETAILED DESCRIPTION OF THE PREFERRED EMBODIMENTS

Figure 4:
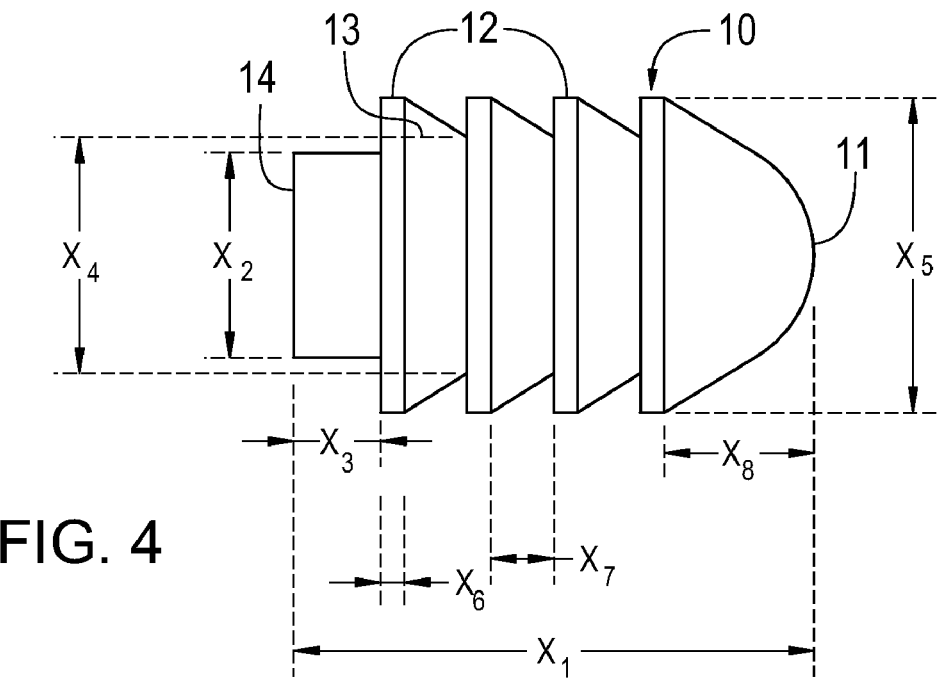
FIG. 4 shows the allograft implant of the present invention.

The system of the present invention for spinal facet joint fusion comprises a bullet-shaped allograft implant 10, best shown in FIG. 4, preferably harvested from human cortical bone. The allograft implant 10 is unidirectional with anti-migration properties that prevent back-out from the point of insertion into the facet joint. The distal end 11 of the implant 10 is convex in shape for easier insertion into the facet joint. Fins 12 on the shaft 13 of the implant 10 provide an increased surface area. The increased surface area provides more area to distribute forces for healing in addition to preventing back-out. Fins 12 allow for increased perfusion of blood around the graft. During the surgical procedure for inserting the implant 10 more blood surrounds the implant 10, which is good for stabilization. The proximal end 14 of the implant 10 is formed with a slightly smaller diameter such that when the implant inserter 50 engages the implant 10, the surgeon will be able to see the entire perimeter of the main body of the implant 10. This permits more accurate placement within the drilled space to hold the implant 10. The allograft implant 10 can be constructed for an interference fit.

An example of the dimensions of the implant 10 is illustrated in FIG. 4, wherein the implant 10 has a length of about 0.3543 inch ($X_1$). The proximal end 14 has a diameter of about 0.1378 inch ($X_2$) and a length of about 0.0591 inch ($X_3$). The shaft 13 has a diameter of about 0.1575 inch ($X_4$). The fins 12 each have a major diameter of about 0.1969 inch ($X_5$) and a lateral edge having a length of about 0.0197 inch ($X_6$). The distance between adjacent lateral edges of the fins 12 is about 0.0394 inch ($X_7$). The convex distal end 11 has a length of about 0.0984 inch ($X_8$).

Figure 1:
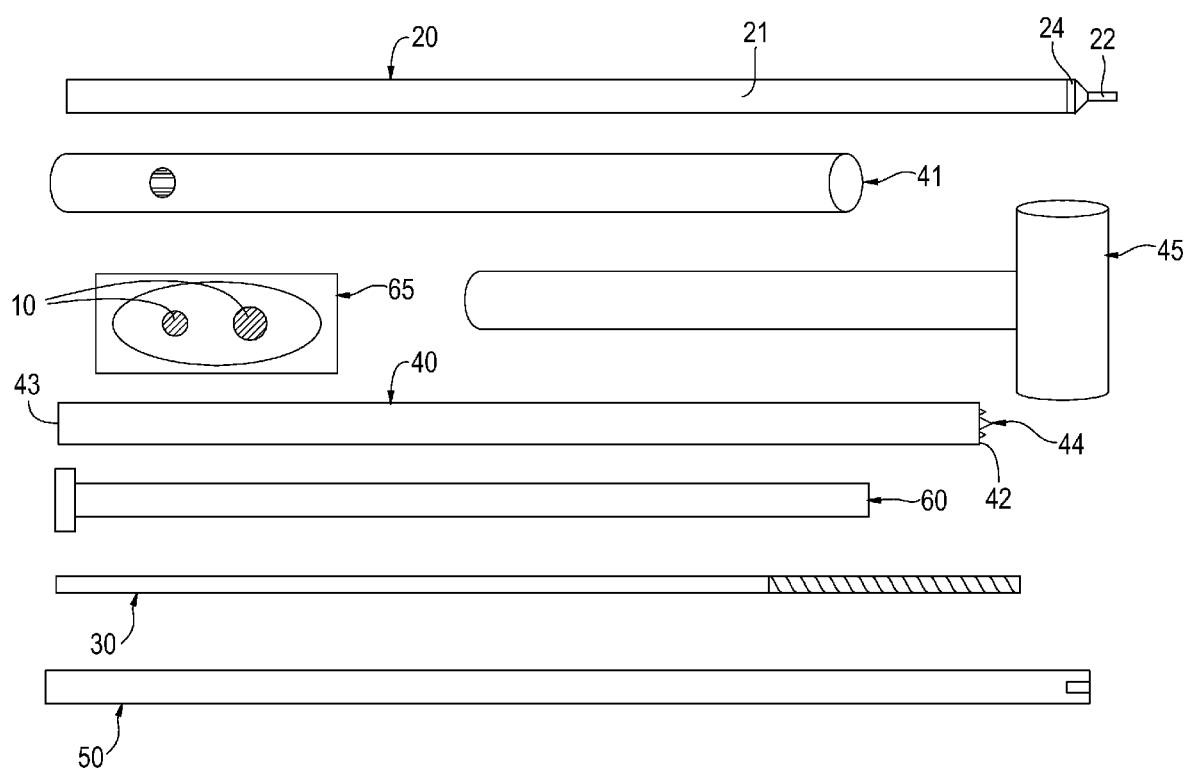
FIG. 1 shows the principal surgical kit components of the present invention.
Figure 2A:
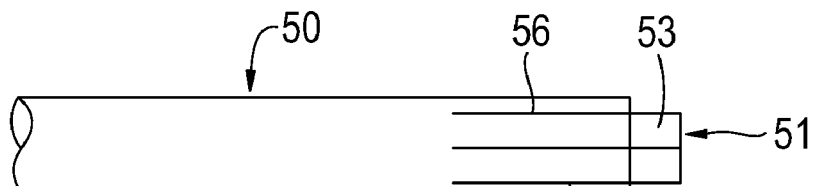
FIG. 2a shows the distal end of the implant inserter.
Figure 2B:
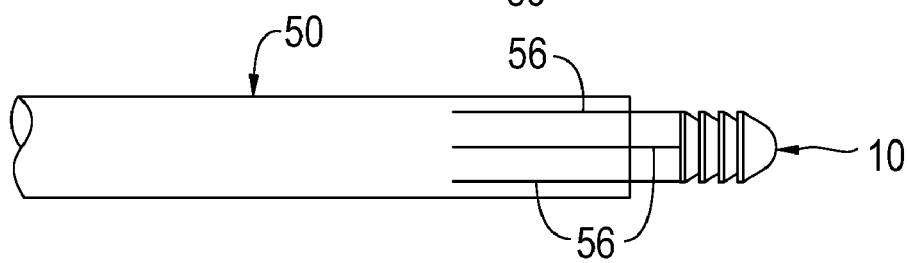
FIG. 2b shows the distal end of the implant inserter having the implant secured thereto.
Figure 3A:
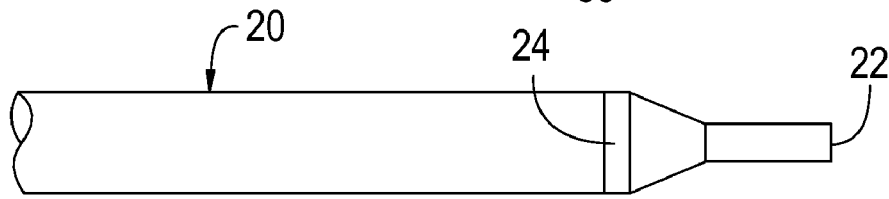
FIG. 3a shows a top view of the distal end of the facet finder.
Figure 3B:
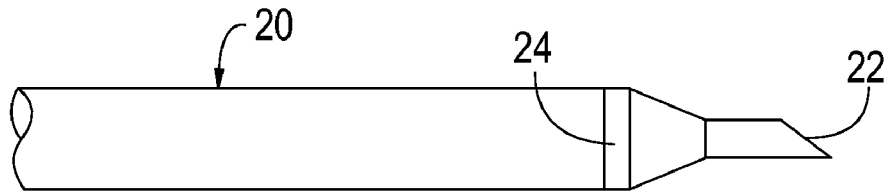
FIG. 3b shows a side view of the distal end of the facet finder.

Several tools, shown in FIGS. 1-3, are used in the methods for inserting the implant 10 into the spinal facets to fuse them. A facet finder 20 will allow for an increase in percutaneous surgeries, which are minimally invasive. For surgeons preferring more open surgery, facet finder 20 may or may not be used; however, it does not preclude a surgeon's choice to do an open procedure. It is not only unnecessary to attempt to distract the facet joint, but it is beneficial to not distract the joint. To this end, the facet finder 20 is useful. Facet finder 20 has a radiolucent body 21 with a radiopaque tip 22 that can be seen on x-ray. Surrounding the distal end of the radiolucent body 21 is a radiopaque band 24. This circular band 24 allows the surgeon to easily target the point of the facet finder 20 using c-arm, fluoroscope, and/or x-ray technology in the operating room and making certain that the radiopaque tip 22 of the facet finder 20 is located exactly in the center of the circle of the radiopaque band 24. This facet finder 20 eliminates the need for a distraction tool.

A drill 30 is provided for drilling a socket of desired depth into the spinal facets. A drill guide 40 is provided that preferably has a depth stop that prevents the drill 30 from advancing too far. The drill guide 40 preferably has a radiolucent handle 41 that is preferably removably and a distal insertion end 42. Drill guide 40 has a proximal end 43 that is made of a material strong enough to withstand light tapping with a surgical mallet 45. For percutlaneous surgery, the distal end 42 of the drill guide 40 has small teeth 44 to lightly engage the drill guide 40 into the facets, once the midline has been determined using the facet finder 20 and fluoroscopy. For open surgery, the distal end 42 of the drill guide 40 preferably has at least 2 teeth 44 that are more aggressive (length and sharpness). The drill guide 40 is tapped into place once the surgeon has visualized the correct placement location for the implant 10.

An allograft inserter 50 is provided to insert the implant 10 into the socket of the facets. The insertion tool 50 has a male-female insertion interface 51 and may include a pusher mechanism to release the implant 10. The insertion tool 50 contains the female portion 53 of the interface 51, with the narrowed proximal end 14 of the implant 10 fitting into the female portion 53 of inserter 50. The insertion tool 50 preferably has a plurality of slits 56 that allow the end of the tool to flex open to receive the proximal end 14 of the implant 10. Once engaged, the insertion tool 50 will be able to hold the implant 10 such that the entire circumference of the implant 10 will be visible to the surgeon. Also, the insertion device 50 may include a positive stop to provide a push-off point so that the inserter 50 can easily place, then disengage, the implant 10 without harming the anti-migration fins 12.

There are two methods for positioning the allograft implant 10 into the socket drilled into the facets. One is a percutaneons or minimally-invasive method, and the other is an open method. In the minimally invasive method the graft site is prepared according to standard procedures. Facet finder 20 is inserted through a standard cannula or facet finder guide 60 to locate the facet joint. Approximation of the midline of the facet joint is made, using fluoroscopy. Drill guide 40 is slid over the facet finder 20 such that the guide 40 is encircling the intended surgical site. Light tapping on top of drill guide 40 with a mallet 45 sets the drill guide 40. The facet finder 20 is removed through the top of the drill guide 40, leaving the engaged drill guide 40 in place. The drill 30 is inserted through the top of the drill guide 40, and the facet joint is drilled to established depth, providing a socket for the implant 10. The drill 30 is removed, leaving the drill guide 40 in place. The implant 10 is placed into the implant loader 65, then loaded into inserter 50. The inserter 50, holding the implant 10, is placed through the drill guide 40 and loaded into the prepared socket. The surgeon taps the inserter 50 until implant 10 reaches the bottom of the prepared socket. The inserter 50 is removed, leaving implant 10 properly placed. The drill guide 40 is removed. Typically, the procedure is repeated with the contralateral facet joint. The patient is closed according to standard procedures.

In the open method the graft site is prepared according to standard procedures. Drill guide 40 is inserted along the plane of the facet joint. Drill guide 40 is firmly seated into place, with the two aggressive teeth 44 engaged in the facet joint. Light tapping on top of drill guide 40 with mallet 45 sets the drill guide 40. The drill 30 is inserted through the top of the drill guide 40, and the facet joint is drilled to established depth, providing a socket for the implant 10. The drill 30 is removed, leaving the drill guide 40 in place. The implant 10 is placed into the implant loader 65, then loaded into inserter 50. The inserter 50, holding the implant 10, is placed through the drill guide 40 and loaded into the prepared socket. The allograft implant 10 is seated using compression until implant 10 is at the bottom of the socket. The inserter 50 is removed, leaving implant 10 properly placed. The drill guide 40 is removed. Typically, the procedure is repeated with the contralateral facet joint. The patient is closed according to standard procedures.

Facet fusion using the methods of the present invention is minimally invasive, even using the open procedure, because less tissue is destroyed in this process than in typical spinal fusion. In many cases, facet fusion by these methods provides pain relief obviating the need for doing traditional spinal fusion and the need for using hardware. However, this facet fusion may also be used as an adjanet to traditional spinal surgery and the use of traditional spinal hardware. The facet fusion can be performed on single or multiple levels (vertebrae). In many cases, this facet fusion can replace rhizotomy facet surgery, which uses radiofrequency to relieve pain, but in the process destroys nerves.

The facet fusion methods of the present invention can stabilize any given spinal segment to reduce painful motion and to accomplish fusion. This spinal stabilization method allows for accelerated rehabilitation, shorter hospital stays, shorter surgical procedures, and reduces muscle, ligament and soft tissue trauma.

Since the facet fusion methods of the present invention are preformed bilaterally, they provide for posterior fusion with two columns of support within the spine. The procedures provide immediate pain relief in many, if not most, cases and are quickly learned by surgeons who do spinal surgeries.

The components of the present invention shown in FIGS. 1-4 can be used to form a facet fusion surgical kit for surgeons to perform facet fusion procedures according to the methods of the present invention.

While the invention has been shown and described in some detail with reference to specific exemplary embodiments, there is no intention that the invention be limited to such detail. On the contrary, the invention is intended to include any alternative or equivalent embodiments that fall within the spirit and scope of the invention as described herein and as recited in the appended claims.

The invention claimed is:

1. A method for fusing a spinal facet joint without distracting the facet joint, comprising the steps of:
   a) locating the facet joint with a facet finder, wherein said facet finder does not distract the facet joint;
   b) sliding a drill guide over said facet finder until a distal end of said drill guide engages the facet joint;
   c) removing said facet finder from within said drill guide;
   d) inserting a drill through said drill guide and drilling a socket within the facet joint to a predetermined depth;
   e) removing said drill from within said drill guide;
   f) securing an unthreaded proximal end of a surgical implant within an unthreaded distal end of an implant inserter, wherein said implant is an unthreaded, cylindrical-shaped allograft implant having a distal end, a plurality of anti-migration fins formed along the length of said implant to secure said implant within the socket, and a reduced diameter proximal end, and wherein said distal end of said implant inserter is operable to receive said reduced diameter proximal end of said implant within said distal end of said implant inserter and thereby reversibly secure said implant to said implant inserter such that the entire circumference of said implant is visible to a surgeon to facilitate insertion of said implant into the socket;
   g) inserting said implant inserter through said drill guide until said distal end of said implant engages the socket;
   h) tapping a proximal end of said implant inserter to push said implant into the socket;
   i) removing said implant inserter from within said drill guide; and
   j) removing said drill guide from the facet joint.

2. A method according to claim 1, wherein said facet finder comprises a radiolucent body having a radiopaque tip, wherein said radiolucent body has a radiopaque band to visually position said radiopaque tip within the center of said radiopaque band to target said radiopaque tip on the facet joint.

3. A method according to claim 1, wherein said proximal end of said implant has a diameter of about 0.1378 inch and said fins each have a diameter of about 0.1969 inch.

4. A surgical kit for use in a method for fusing a spinal facet joint without distracting the facet joint, comprising:
   a) a surgical implant, wherein said implant is an unthreaded, cylindrical-shaped allograft implant having a distal end, a plurality of anti-migration fins formed along the length of said implant to secure said implant within a socket formed in the facet joint, and a reduced diameter proximal end;
   b) a facet finder for locating the facet joint without distracting the facet joint;
   c) a drill for creating the socket in the facet joint for receiving said implant;
   d) a drill guide; and
   e) an implant inserter for inserting said implant into the socket, wherein said implant inserter has an unthreaded distal end operable to receive said reduced diameter proximal end of said implant within said distal end of said implant inserter and thereby reversibly secure said implant to said implant inserter such that the entire circumference of said implant is visible to a surgeon to facilitate insertion of said implant into the socket.

5. A surgical kit according to claim 4, wherein said facet finder comprises a radiolucent body having a radiopaque tip, wherein said radiolucent body has a radiopaque band to visually position said radiopaque tip within the center of said radiopaque band to target said radiopaque tip on the facet joint.

6. A surgical kit according to claim 4, wherein said proximal end of said implant has a diameter of about 0.1378 inch and said fins each have a diameter of about 0.1969 inch.

* * * * *